(12) United States Patent
Melton et al.

(10) Patent No.: US 7,983,777 B2
(45) Date of Patent: Jul. 19, 2011

(54) SYSTEM FOR BIOMEDICAL IMPLANT CREATION AND PROCUREMENT

(76) Inventors: Mark Melton, Carlsbad, CA (US); Anthony James, Bartlett, TN (US); Steve Bruneau, Edgewater Park, NJ (US); Thomas W. Rassmann, Marlton, NJ (US); Jonathan D. Langlois, Wilton, NY (US)

( * ) Notice: Subject to any disclaimer, the term of this patent is extended or adjusted under 35 U.S.C. 154(b) by 1247 days.

(21) Appl. No.: 11/506,575

(22) Filed: Aug. 18, 2006

(65) Prior Publication Data

US 2007/0203605 A1    Aug. 30, 2007

Related U.S. Application Data

(60) Provisional application No. 60/709,979, filed on Aug. 19, 2005.

(51) Int. Cl.
G06F 19/00 (2006.01)
G06Q 30/00 (2006.01)
A61F 2/82 (2006.01)

(52) U.S. Cl. ......... 700/98; 700/118; 705/26.5; 623/1.15
(58) Field of Classification Search .................... 700/98, 700/118; 705/26; 623/1.15
See application file for complete search history.

(56) References Cited

U.S. PATENT DOCUMENTS

| | | | |
|---|---|---|---|
| 5,098,383 A | 3/1992 | Hemmy et al. |
| 5,365,996 A | 11/1994 | Crook |
| 5,452,407 A | 9/1995 | Crook |
| 5,768,134 A | 6/1998 | Swaelens et al. |
| 5,871,018 A | 2/1999 | Delp et al. |
| 5,885,296 A | 3/1999 | Masini |
| 6,112,109 A | 8/2000 | D'Urso |
| 6,205,411 B1 | 3/2001 | DiGioia, III et al. |
| 6,254,639 B1 | 7/2001 | Peckitt |
| 6,295,513 B1 | 9/2001 | Thackston |
| 6,327,491 B1 | 12/2001 | Franklin et al. |
| 6,381,029 B1 | 4/2002 | Tipirneni |
| 6,463,351 B1 | 10/2002 | Clynch |

(Continued)

FOREIGN PATENT DOCUMENTS

EP    1 226 788 A1    7/2002

(Continued)

OTHER PUBLICATIONS

Radermacher, et al., "Computer Assisted Orthopaedic Surgery With Image Based Individual Templates", *Clinical Orthopaedics and Related Research* No. 354, pp. 28-38, 1998 Lippincott Williams & Wilkins.

(Continued)

*Primary Examiner* — Thomas J Sweet
*Assistant Examiner* — Matthew Schall
(74) *Attorney, Agent, or Firm* — Kilpatrick Townsend & Stockton LLP (57) ABSTRACT

Automated systems and methods for creating and obtaining devices, including biomedical implants. Systems can have a surgeon's device, an automated platform, and a server. The surgeon's device can send a request for a template of a biomedical implant, and can access tools to edit the template. The automated platform can receive the edited template, and can generate a response. The response can include translating the edited template into a design for a biomedical implant. The response can further include generating a notice if the edited template falls outside of an acceptable range, or if the edited template is similar to the design of a standard biomedical implant. There can also be provided a manufacturing facility that can manufacture the implant and send the implant to the surgeon.

48 Claims, 11 Drawing Sheets

U.S. PATENT DOCUMENTS

| | | |
|---|---|---|
| 6,503,249 B1 | 1/2003 | Krause |
| 6,772,026 B2 | 8/2004 | Bradbury et al. |
| 6,786,930 B2 | 9/2004 | Biscup |
| 6,798,533 B2 | 9/2004 | Tipirneni |
| 6,821,123 B2 | 11/2004 | Andersson et al. |
| 6,827,723 B2 | 12/2004 | Carson |
| 6,837,892 B2 | 1/2005 | Shoham |
| 6,859,661 B2 | 2/2005 | Tuke |
| 6,882,982 B2 | 4/2005 | McMenimen et al. |
| 6,905,514 B2 | 6/2005 | Carignan et al. |
| 6,923,817 B2 | 8/2005 | Carson et al. |
| 7,035,702 B2 | 4/2006 | Jelonek et al. |
| 7,162,322 B2 | 1/2007 | Arbogast et al. |
| 7,180,624 B2 | 2/2007 | Tipirneni |
| 7,319,540 B2 | 1/2008 | Tipirneni |
| 7,340,316 B2 | 3/2008 | Spaeth et al. |
| 7,468,075 B2 | 12/2008 | Lang et al. |
| 7,517,365 B2 | 4/2009 | Carignan et al. |
| 2002/0007294 A1 | 1/2002 | Bradbury et al. |
| 2002/0018981 A1 | 2/2002 | Andersson et al. |
| 2002/0072821 A1 | 6/2002 | Baker |
| 2002/0115934 A1 | 8/2002 | Tuke |
| 2002/0133175 A1 | 9/2002 | Carson |
| 2002/0147455 A1 | 10/2002 | Carson |
| 2003/0055502 A1 | 3/2003 | Lang et al. |
| 2003/0069591 A1 | 4/2003 | Carson |
| 2003/0216669 A1 | 11/2003 | Lang |
| 2004/0133276 A1 | 7/2004 | Lang |
| 2004/0138754 A1 | 7/2004 | Lang |
| 2004/0204644 A1 | 10/2004 | Tsougarakis et al. |
| 2004/0204760 A1 | 10/2004 | Fitz |
| 2004/0236424 A1 | 11/2004 | Berez |
| 2004/0243481 A1 | 12/2004 | Bradbury et al. |
| 2005/0113846 A1 | 5/2005 | Carson |
| 2005/0119777 A1 | 6/2005 | Arbogast et al. |
| 2005/0137599 A1 | 6/2005 | Masini |
| 2005/0148843 A1 | 7/2005 | Roose |
| 2005/0197569 A1 | 9/2005 | McCombs |
| 2005/0203384 A1 | 9/2005 | Sati et al. |
| 2005/0209605 A1 | 9/2005 | Grimm et al. |
| 2005/0209726 A1 | 9/2005 | Voit et al. |
| 2005/0216305 A1 | 9/2005 | Funderud |
| 2005/0234332 A1 | 10/2005 | Murphy |
| 2005/0234461 A1 | 10/2005 | Burdulis et al. |
| 2005/0234468 A1 | 10/2005 | Carson |
| 2005/0267353 A1 | 12/2005 | Marquart et al. |
| 2005/0267584 A1 | 12/2005 | Burdulis et al. |
| 2006/0064105 A1 | 3/2006 | Raistrick et al. |
| 2006/0161051 A1 | 7/2006 | Terrill-Grisoni et al. |
| 2006/0190011 A1 | 8/2006 | Ries |
| 2006/0195048 A1 | 8/2006 | Leitner et al. |
| 2006/0200025 A1 | 9/2006 | Elliott et al. |
| 2006/0217732 A1 | 9/2006 | Seo et al. |
| 2007/0015995 A1 | 1/2007 | Lang et al. |
| 2007/0038059 A1 | 2/2007 | Sheffer et al. |
| 2007/0038223 A1 | 2/2007 | Marquart et al. |
| 2007/0055268 A1 | 3/2007 | Utz et al. |
| 2007/0066917 A1 | 3/2007 | Hodorek et al. |
| 2007/0067032 A1 | 3/2007 | Felt et al. |
| 2007/0073305 A1 | 3/2007 | Lionberger et al. |
| 2007/0073306 A1 | 3/2007 | Lakin et al. |
| 2007/0081713 A1 | 4/2007 | Jerebko |
| 2007/0083266 A1 | 4/2007 | Lang |
| 2007/0100462 A1 | 5/2007 | Lang |
| 2007/0118055 A1 | 5/2007 | McCombs |
| 2007/0156171 A1 | 7/2007 | Lang |
| 2007/0198022 A1 | 8/2007 | Lang et al. |
| 2007/0226986 A1 | 10/2007 | Park |
| 2007/0233141 A1 | 10/2007 | Park |
| 2007/0233269 A1 | 10/2007 | Steines |
| 2007/0250169 A1 | 10/2007 | Lang |
| 2007/0288030 A1 | 12/2007 | Metzger et al. |
| 2008/0161815 A1 | 7/2008 | Schoenefeld et al. |
| 2008/0215059 A1 | 9/2008 | Carignan et al. |
| 2008/0243127 A1 | 10/2008 | Lang et al. |
| 2008/0262624 A1 | 10/2008 | White et al. |
| 2008/0281329 A1 | 11/2008 | Fitz et al. |
| 2008/0281426 A1 | 11/2008 | Fitz et al. |
| 2008/0319491 A1 | 12/2008 | Schoenefeld |
| 2009/0024131 A1 | 1/2009 | Metzger et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088763 A1 | 4/2009 | Aram et al. |
| 2009/0099567 A1 | 4/2009 | Zajac |

FOREIGN PATENT DOCUMENTS

| | | |
|---|---|---|
| EP | 1 226 788 B1 | 7/2002 |
| EP | 1226788 A1 | 7/2002 |
| EP | 1 406 203 A2 | 4/2004 |
| EP | 1 406 203 A3 | 4/2004 |
| EP | 1406203 B1 | 8/2006 |
| EP | 1226788 B1 | 10/2006 |
| JP | 2002-304439 | 10/2002 |
| WO | WO 03/006107 A1 | 1/2003 |
| WO | WO 03/030787 | 4/2003 |
| WO | WO 03/065931 | 8/2003 |
| WO | WO 2004/019792 A1 | 3/2004 |
| WO | WO 2004019792 A1 | 3/2004 |
| WO | WO 2004/069036 A2 | 8/2004 |
| WO | WO 2004/070580 A2 | 8/2004 |
| WO | WO 2004069036 A2 | 8/2004 |
| WO | WO 2004070580 A2 | 8/2004 |
| WO | WO 2005/057439 A1 | 6/2005 |

OTHER PUBLICATIONS

Hafez, et al., 'Computer-assisted Total Knee Arthroplasty Using Patient-specific Templating,' *Clinical Othopaedics and Related Research*, No. 444, 184-192 (2008).

International Search Report and Written Opinion in related Application No. PCT/US07/18260.

Notice to File Corrected Application Papers dated Aug. 3, 2010 in related U.S. Appl. No. 12/839,433 and Response thereto.

SYSTEM FOR BIOMEDICAL IMPLANT CREATION AND PROCUREMENT

RELATED APPLICATIONS

This invention claims priority to U.S. provisional patent application No. 60/709,979, entitled "SYSTEM FOR BIOMEDICAL DEVICE CREATION AND PROCUREMENT," filed on Aug. 19, 2005, the entirety of which is hereby incorporated by reference.

RELATED FIELDS

This invention relates to a system that can be used to create and order devices, such as biomedical implants.

BACKGROUND OF THE INVENTION

Surgeons routinely implant biomedical implants, including but not limited to intramedullary nails or hip stems, into patients. For example, a patient might have fractured his or her leg after falling. Another patient might have conditions typically associated with old age, for example, a weakened hip. A surgeon might decide that the patient's condition requires treatment with one or more biomedical implants. There are companies that manufacture and sell biomedical implants in standard sizes and designs. Sometimes, these standard implants are appropriate for the patient's condition. The surgeon could simply purchase the standard implant to treat the patient's condition. But oftentimes, these standard biomedical implants are not appropriate for treatment of the patient's condition. For example, if a patient has a fractured leg, the fracture might be larger, wider, or otherwise differently shaped than is appropriate for a standard biomedical implant. The standard biomedical implant might not fit into the fracture, might not make contact at the required points, or might otherwise inhibit the treatment of the patient's condition.

When a standard biomedical implant is not appropriate for treatment, the surgeon can order a customized biomedical implant. Customized implants provide the flexibility of selecting an implant with the appropriate design to treat the patient's condition. Traditionally, biomedical implant manufacturers collaborate with a surgeon to design a customized implant. In this traditional method, all communication between the requesting surgeon and the biomedical implant manufacturer is either oral or written and delivered through the postal service. If the communication is oral, then the surgeon must schedule an appointment with the implant manufacturer, either by telephone or in person. Accordingly, communication can only occur when the manufacturer and surgeon are available at the same time. Waiting on concurrent availability takes a long time, and the delay might affect the patient's condition. Collaboration in these traditional methods of design also occurs in writing and is delivered through the postal service. For example, a surgeon might send X-rays and order forms through the mail, and the implant manufacturer will mail the design proposals back to the surgeon. Sending communication through the mail is time consuming, and the delay might affect the patient's condition. Accordingly, traditional systems and methods that depend on oral communication, or written communication delivered by the postal service, is undesirable.

SUMMARY OF THE INVENTION

Embodiments of the invention provide for systems and methods of creating and obtaining biomedical implants. Certain embodiments can be provided with a device for a surgeon, which can be embodied as a computer, facsimile machine, handheld computing device, or a telephone system, if desired. Other embodiments can have an automated platform for an implant manufacturer, which can also be embodied as a computer, facsimile machine, handheld computing device, or a telephone system, if desired. Embodiments include a server to allow the surgeon's device and the automated platform to transmit information over a network. In some embodiments, the network can be the Internet while in others, the network could be an Intranet. Certain embodiments further include a manufacturing facility. The manufacturing facility can receive instructions to manufacture the implant, and can then send the implant to the surgeon.

The surgeon's device can be provided with tools, or can have access to tools, to enable the surgeon to practice certain methods of the invention. The tools can be embodied as software loaded on a computer, if the surgeon's device is embodied as a computer. In an alternative embodiment, the tools can be provided on the automated platform or on a server, and can be accessible by the surgeon's device. If desired, the tools can be other known embodiments such as menu selections on a telephone system. One tool can allow a surgeon to transmit a request for a biomedical implant. Tools of other embodiments can enable the surgeon to edit templates that represent biomedical implants. Embodiments further enable the surgeon to upload or input information into the surgeon's device, such as diagnostic data and patient information, if desired. Certain embodiments enable the surgeon's device to either send or receive information.

Embodiments can include a server to receive and transmit information between the surgeon's device and the automated platform, if provided in the embodiment. If desired, the server can transmit information over the Internet. The server and the automated platform can be housed in the same location, or can be housed in different locations. In some embodiments, the server and the automated platform can be members of the same element, or the server and the automated platform can be separate elements.

Embodiments of the invention may include an automated platform that can be accessed by a biomedical implant manufacturer. The automated platform can be embodied as a computer, if desired, and can also be embodied as a facsimile machine, handheld computing device, or a telephone system. In certain embodiments there are tools associated with the automated platform, and the tools can include computer aided design ("CAD") systems. The CAD systems can be enabled to translate edits received from the surgeon's device into a design for an implant. In some embodiments, memory can be provided. The automated platform can access the memory, but the automated platform and the memory need not be members of the same element. The memory can include multiple types of information, including a collection of templates, ranges of acceptable design parameters for implants, or designs of standard implants.

In some embodiments, there is provided a manufacturing facility. The manufacturing facility can receive manufacturing instructions from the automated platform. The manufacturing facility and the automated platform can communicate through the server, or by other means including the postal service or telephone system. The manufacturing facility can have known manufacturing tools, and can manufacture the implant. If desired, the manufacturing facility can send the implant to the surgeon.

It is accordingly an aspect of some embodiments of the invention to provide systems and methods for creating and obtaining devices, including biomedical implants.

It is an additional aspect of some embodiments of the invention to provide systems and methods that quickly and efficiently create implants.

It is an additional aspect of some embodiments of the invention to provide systems and methods that create implants without the need for diagnostic data.

It is an additional aspect of some embodiments of the invention to provide systems and methods that allow a surgeon and an implant manufacturer to collaborate on a proposed implant design.

It is an additional aspect of some embodiments of the invention to provide systems and methods that allow a surgeon who is unskilled in CAD systems to contribute to a proposed implant design.

It is an additional aspect of some embodiments of the invention to provide systems and methods that record pertinent information about design iterations.

Other aspects, features, and advantages of embodiments of the invention will become apparent with respect to the remainder of this document.

DETAILED DESCRIPTION OF THE DRAWINGS

Figure 1:
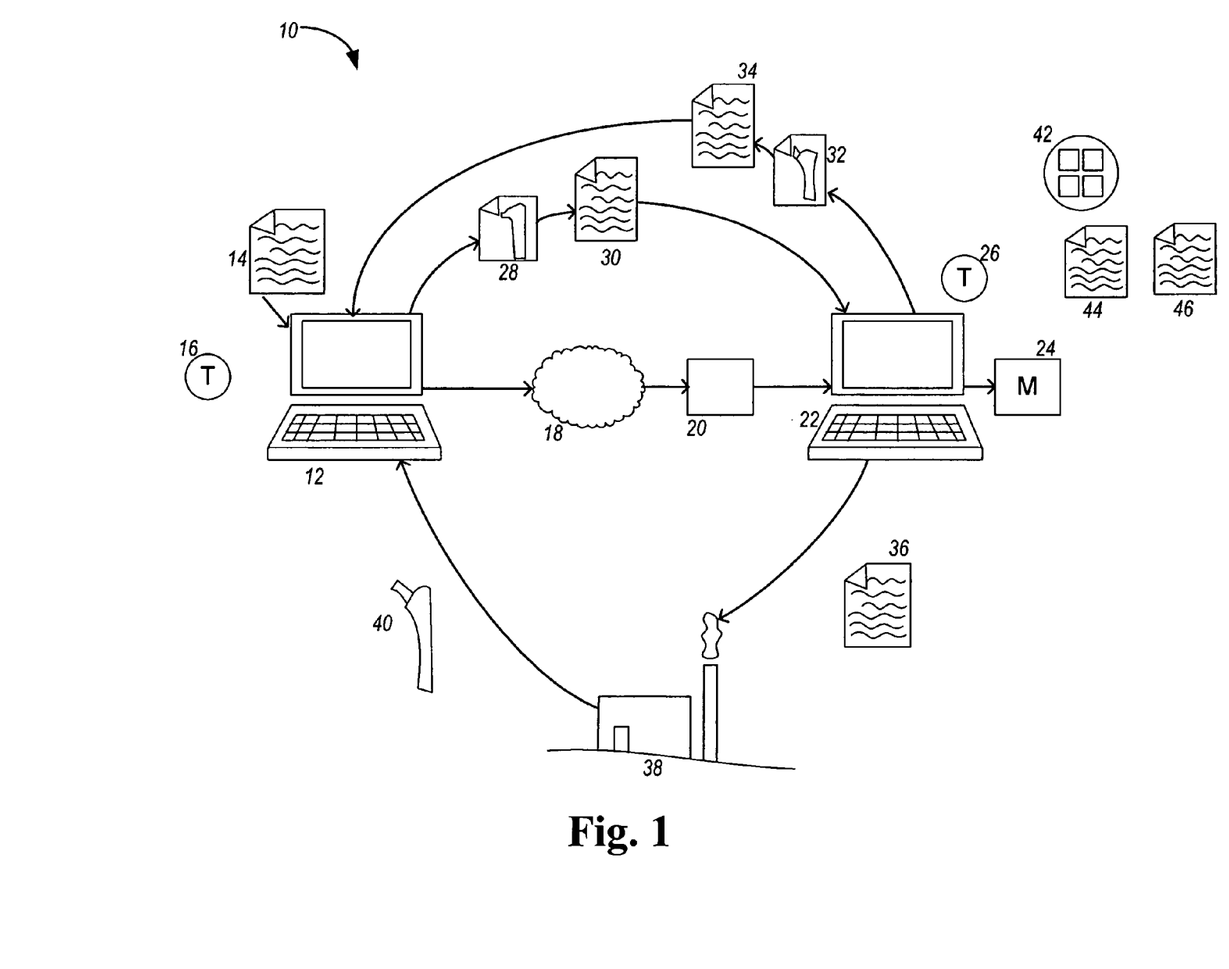
FIG. 1 illustrates an embodiment of a system that can be used to practice an embodiment of a method of this invention.
Figure 2:
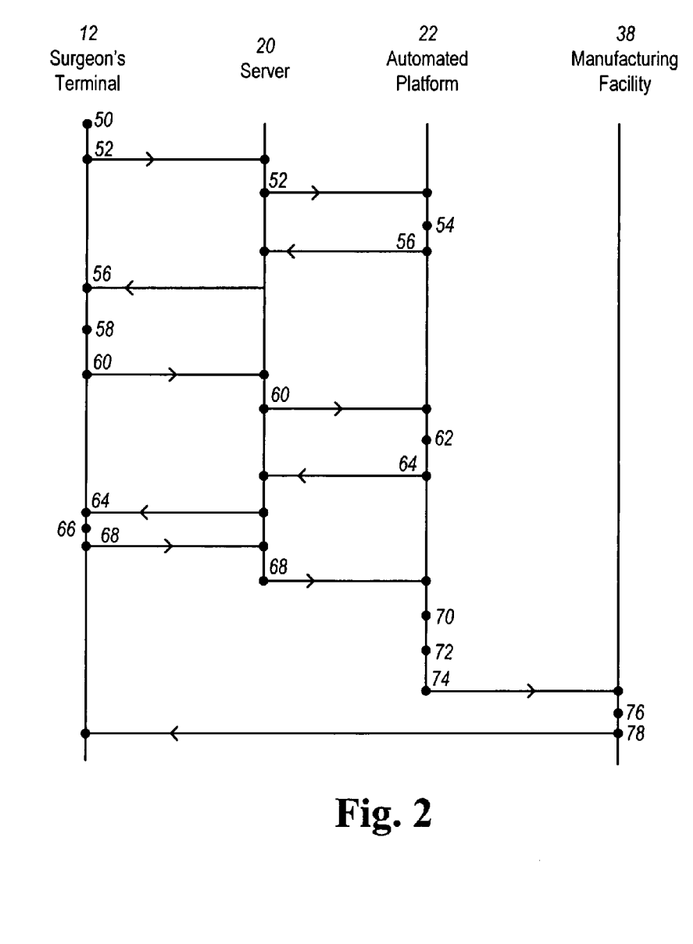
FIG. 2 illustrates an embodiment of the method in FIG. 1.
Figure 3:
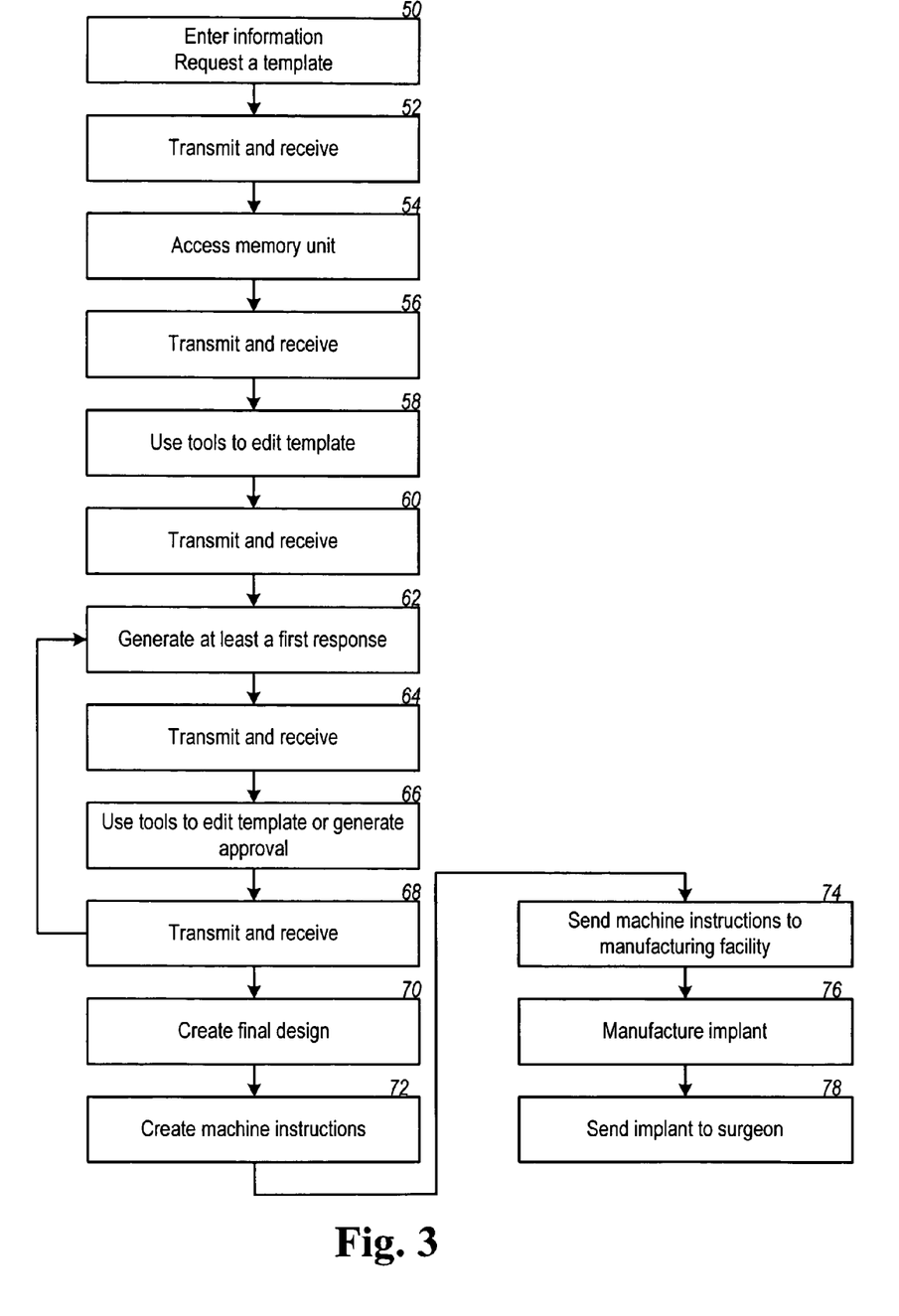
FIG. 3 is another illustration of the method in FIG. 2.

Embodiments of the invention provide systems and methods for creating and obtaining devices, including biomedical implants. Referring now to FIGS. 1-3, systems 10 of certain embodiments can be provided with a surgeon's device 12. In FIG. 1, the surgeon's device 12 is embodied as a computer, but other embodiments can include a facsimile machine, a telephone, a handheld computing device, or a pager. The surgeon's device 12 can access a tool 16 to input information 14. The tool 16 can be provided on the surgeon's device 12, or can be provided on the automatic platform 22 or the server 20 and can be accessible by the surgeon's device 12. Information 14 can include identifying information for the surgeon and/or the patient, including names, case numbers, and insurance information, if desired. In certain embodiments, information 14 can include diagnostic data, such as a digital X-ray image, a magnetic resonance image ("MRI"), or a computer tomography ("CT") image.

Figure 6:
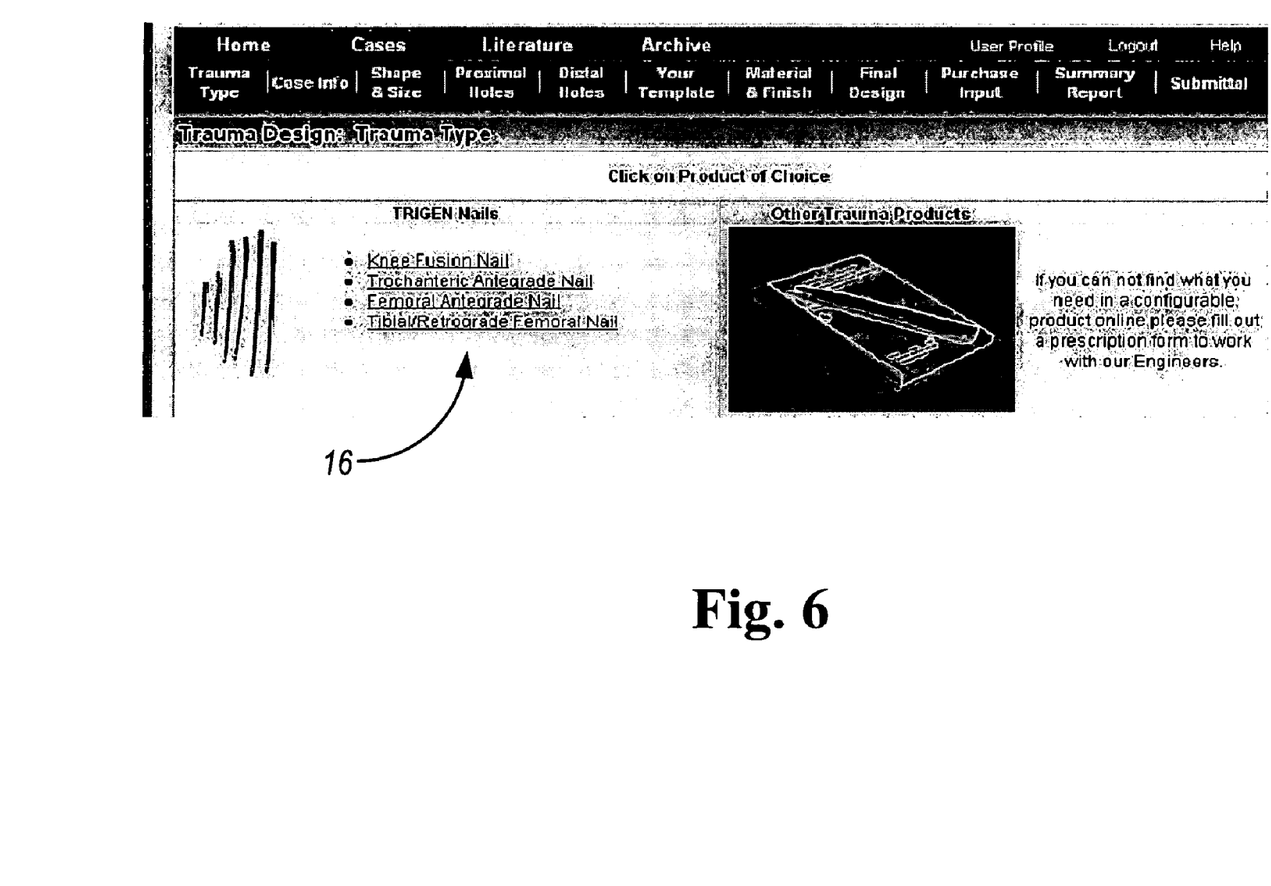
FIG. 6 illustrates an embodiment of a tool to send a request for a biomedical implant.

The surgeon's device 12 can access other tools 16 to practice other methods of the invention. The tools 16 can be provided on the surgeon's device 12, or can be provided on the automatic platform 22 or the server 20 and can be accessible by the surgeon's device 12. One tool 16 can enable the surgeon to send a request 28 for a template 32 that represents a biomedical implant, or for an accessory to a biomedical implant. FIG. 6 illustrates one embodiment of a tool 16 to send a request 28 for template 32 of an intramedullary nail. The tool 16 provides a choice of four types of nails: a knee fusion nail, a trochanteric antegrade nail, a femoral antegrade nail, and a tibial/retrograde femoral nail. Other types of implants are also included in embodiments of the invention. For example, embodiments can provide implants for different types of hip stems, or for cosmetic implants such as breast implants. Embodiments can also provide accessories or customized instruments to implant the implants. For example, sometimes when a surgeon installs a custom-designed implant, the surgeon requires special tools. Accordingly, embodiments of systems 10 can provide accessories to help the surgeon install the biomedical implant. For example, there can be provided drills, drill guides, broaches, nail guide drops, nail guide handles, proximal entry reamers, reamer drills, hexdrivers, drill sleeves, guide bolts, targeters, or other accessories known in the art. Further, embodiments of the invention can provide templates for trays in which to house accessories and/or biomedical implants. Accordingly, the surgeon's request 28 can include multiple types of implants, or accessories for implants, or trays for implants.

Certain embodiments also provide tools 16 for editing at least one design parameter of a template 32. The tools 16 can be provided on the surgeon's device 12, or can be provided on the automatic platform 22 or the server 20 and can be accessible by the surgeon's device 12. There can be many design parameters associated with various templates 32. For example, if the implant is for an intramedullary nail, as in FIG. 9, examples of design parameters can include length, outside diameter, bow radius, hole size, hole location, hole angle, the number of holes, slot size, slot location, material, surface finish, or surface coating. If the implant is for a hip stem, as in FIG. 8, examples of design parameters can include the profile, stem size, length, head offset, neck height, neck angle, medial and lateral fill, posterior and anterior fill, shoulder height, beam thickness, material, surface finish, or surface coating.

Figure 7:
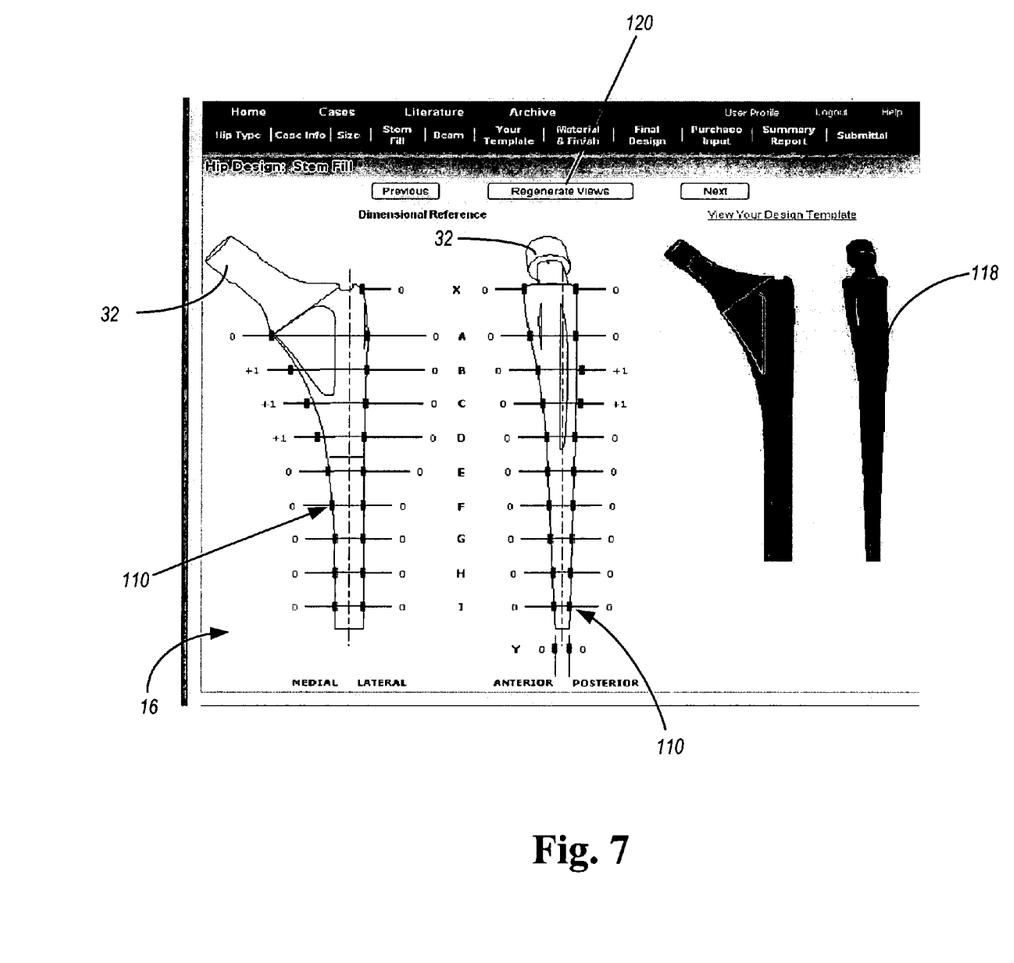
FIG. 7 illustrates an embodiment of a tool for editing a hip stem template, where the tool comprises at least one slideable bar.

One embodiment of tool 16 for editing is illustrated in FIG. 7 and can include at least one slideable bar 110 associated with an edge of the template 32. The surgeon can click and drag the slideable bar 110 to adjust design parameters of the template 32. As illustrated in FIG. 7, the slideable bars 110 can adjust the width and depth of the template 32. In other embodiments, the slideable bars 110 can adjust the height or other design parameters of the template 32. The invention is not limited to a slideable bar 110, but can also include slideable points, or any other shaped sliding element.

Figure 8:
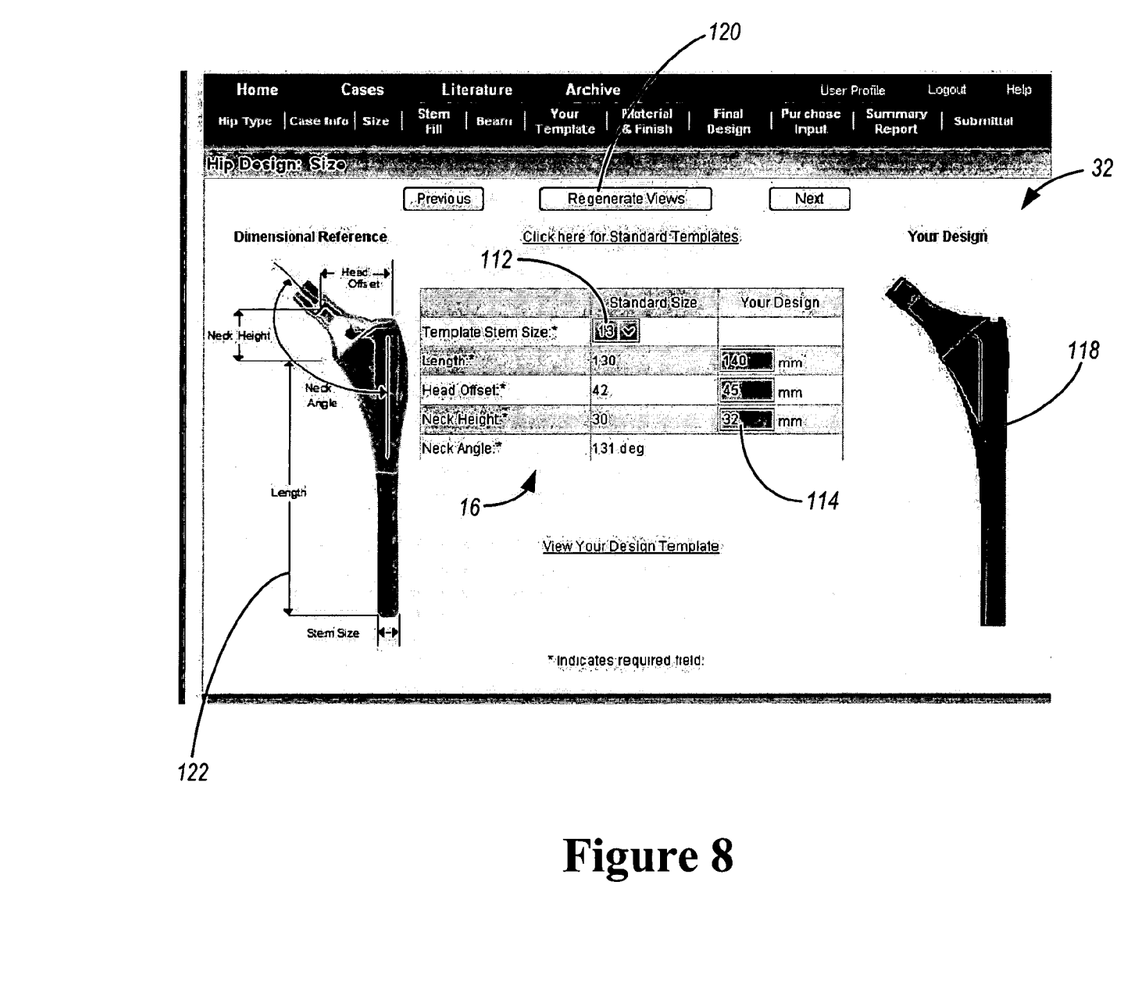
FIG. 8 illustrates an embodiment of a tool for editing a hip stem template, where the tool comprises at least one form to input design parameters.
Figure 9:
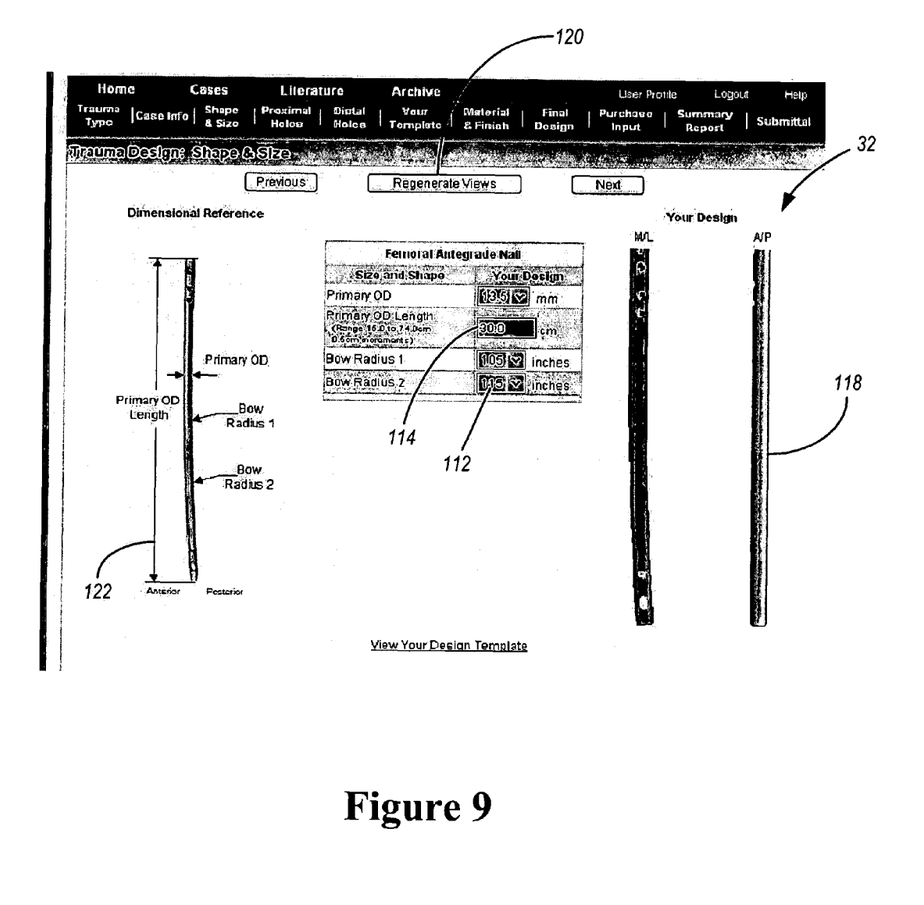
FIG. 9 illustrates an embodiment of a tool for editing an intramedullary nail, where the tool comprises at least one form to input design parameters.
Figure 10:
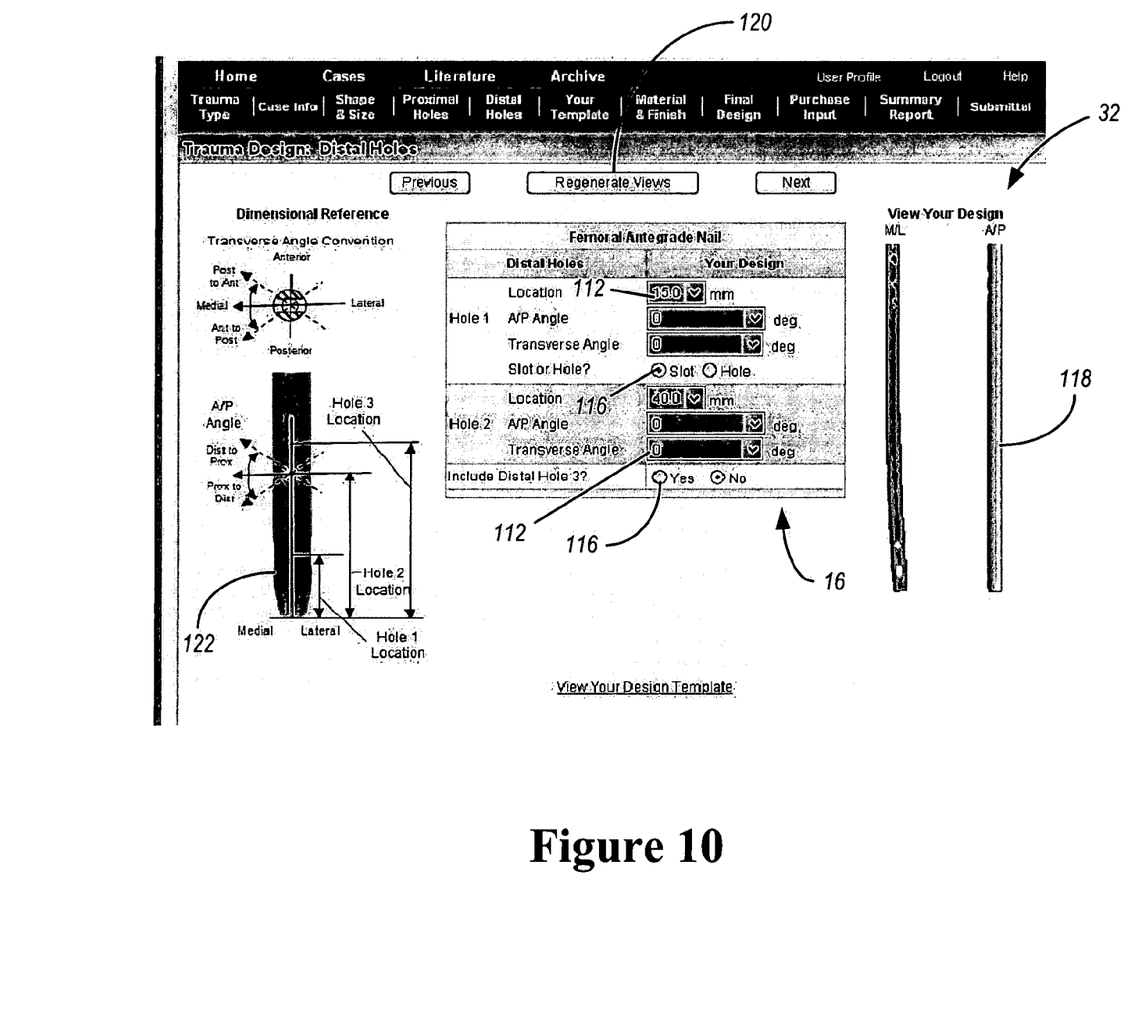
FIG. 10 illustrates another embodiment of the tool in FIG. 9.

In the embodiment illustrated in FIGS. 8-10, the tool 16 can include a form to input at least one design parameter. There can be at least three types of forms: a menu 112, a blank field 114, or a selector 116. If the form is embodied as a menu 112, the surgeon can click on the down arrow to obtain a list of design parameters, and can click on the desired design parameter of his/her choice. In FIG. 9, there is provided three menus 112, two of which are consecutive. In certain embodiments, menus 112 can be interrelated such that their design parameters depend on one another. In these embodiments, the design parameters presented for selection in the second menu 112 depend on the design parameters that the surgeon selected in the first menu 112. For example, if in the first menu 112 the surgeon selected an outside diameter of 10 mm, then the choices for an inside diameter provided in the second menu 112 would be less than 10 mm. If the form is embodied as a blank field 114, the surgeon can type in the desired design parameter into the blank field 114. Still another embodiment of a tool 16 is a selector 116 for the surgeon to select design parameters. In FIG. 10, there are two selectors 116 and each selector 116 only provides two choices. In other embodiments, there can be multiple selectors 116 and each selector 116 can provide multiple choices. Accordingly, the tool 16 for editing can include at least one of a slideable bar 110, a menu 112, a blank field 114, a selector 116, or a combination of any of these.

The embodiments in FIGS. 8-10 illustrate a dimensional reference 122, which can serve as a guide while the surgeon is editing the template 32. For example, the dimensional reference 122 shown in FIG. 8 illustrates design parameters including head offset, neck height, neck angle, length, and stem size. The dimensional reference 122 helps the surgeon to identify design parameters while he/she is editing the template 32.

Other embodiments of the surgeon's device 12 also access tools 16 for creating a design based on diagnostic data 14. As discussed above, diagnostic data 14 can include X-rays, MRI images, or CT images. In some embodiments, the tools 16 can enable the surgeon to select certain points or elements associated with the diagnostic data 14. The automated platform 22 can be provided with tools 26 to translate the selected points into a design. For example, there could be an X-ray showing a fractured leg, and the surgeon can select two points on one side of the fracture, and one point on the other side of the fracture. The automated platform 22 could translate those points into a design for an intramedullary nail.

In some embodiments a working model 118 can be provided on the surgeon's device 12 to allow the surgeon to view the progress of the design, and to catch any potential mistakes. The surgeon can enter edits, and can select a regeneration button 120 to update the working model 118. Alternatively, the working model 118 can be regenerated automatically whenever the surgeon edits the template 32. For example, in FIG. 8 the standard length is 130 mm, and the edited length is 140 mm. When the regeneration button 120 is selected, the working model 118 will grow 10 mm in length. If the surgeon made a mistake while entering edits, then the mistake can be illustrated on the working model 118. For example, if the length was 130 mm, and the surgeon mistakenly entered 1300 mm, then the surgeon can catch the mistake by viewing the working model 118.

Figure 11:
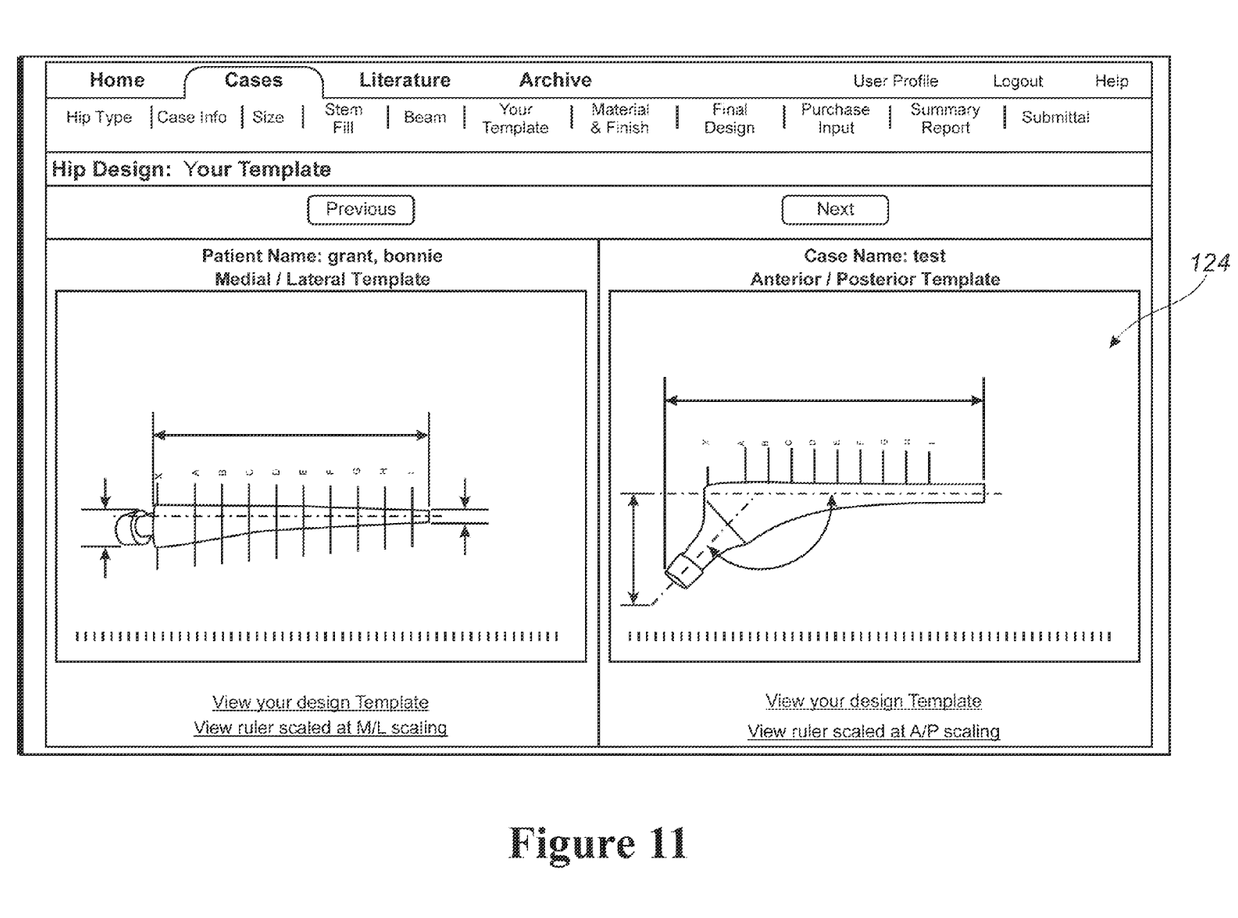
FIG. 11 illustrates an embodiment of a tool to compare diagnostic data with a design for a biomedical implant.

In addition, some embodiments of the surgeon's device 12 can include a comparison tool 124 to allow the surgeon to compare the design to diagnostic data (not shown), such as an X-ray of the patient, to the design for the implant. This comparison tool 124 is helpful because it allows the surgeon to determine whether the design is appropriate for treatment of the patient's condition. The embodiment of the comparison tool 124 illustrated in FIG. 11 is a printable illustration of the design scaled to fit the diagnostic data. Other embodiments of the comparison tool 124 are within embodiments of the invention. In FIG. 11, there is one printable illustration for the medial and lateral side of the implant, and another printable illustration for the anterior and posterior side of the implant. The surgeon can print out the illustrations and compare them to the diagnostic data. If the design on the illustrations does not fit the diagnostic data, then the surgeon can use the tools 16 for editing and redesign the implant.

Certain embodiments can include a server 20. The server 20 can be embodied as a computer, if desired. The server 20 can be enabled to receive and transmit information between at least the surgeon's device 12 and the automated platform 22. The server 20 can transmit information over a network 18, which can be embodied as the Internet, or as an Intranet.

Other embodiments can include an automated platform 22. The automated platform 22 can be accessed by a biomedical implant manufacturer to practice methods of the invention. In FIG. 1, the automated platform 22 is embodied as a computer, but other embodiments are also within the scope of the invention. The server 20 and the automated platform 22 can be housed in the same location, or can be housed in different locations, if desired. In the embodiment shown in FIG. 1, the server 20 and the automated platform 22 are two separate elements, but in other embodiments, the server 20 and the automated platform 22 can be members of the same element. In some embodiments, memory 24 can be provided. The memory 24 can be a hard drive of a computer, if desired, but other embodiments are within the scope of the invention. The automated platform 22 can access the memory 24, but the automated platform 22 and the memory 24 need not be members of the same element. The memory 24 can store multiple types of information, including a collection of templates 42, ranges of acceptable design parameters for implants 44, or designs of standard implants 46.

Embodiments of the automated platform 22 can be provided with tools 26 to automatically generate certain responses to the edits 30 received from the surgeon's device 12. In some embodiments the tools 26 can include computer aided design ("CAD") systems. Common CAD systems known in the art can include SolidWorks®, produced by SolidWorks Corporation, 300 Baker Avenue, Concord, Mass. 01742, or Pro Engineer®, produced by Parametric Technology Corporation, 140 Kendrick Street, Needham, Mass. 02494. The CAD systems can be enabled to translate edits 30 of the template 32 received from the surgeon's device 12 into a design for an implant 34.

Figure 4:
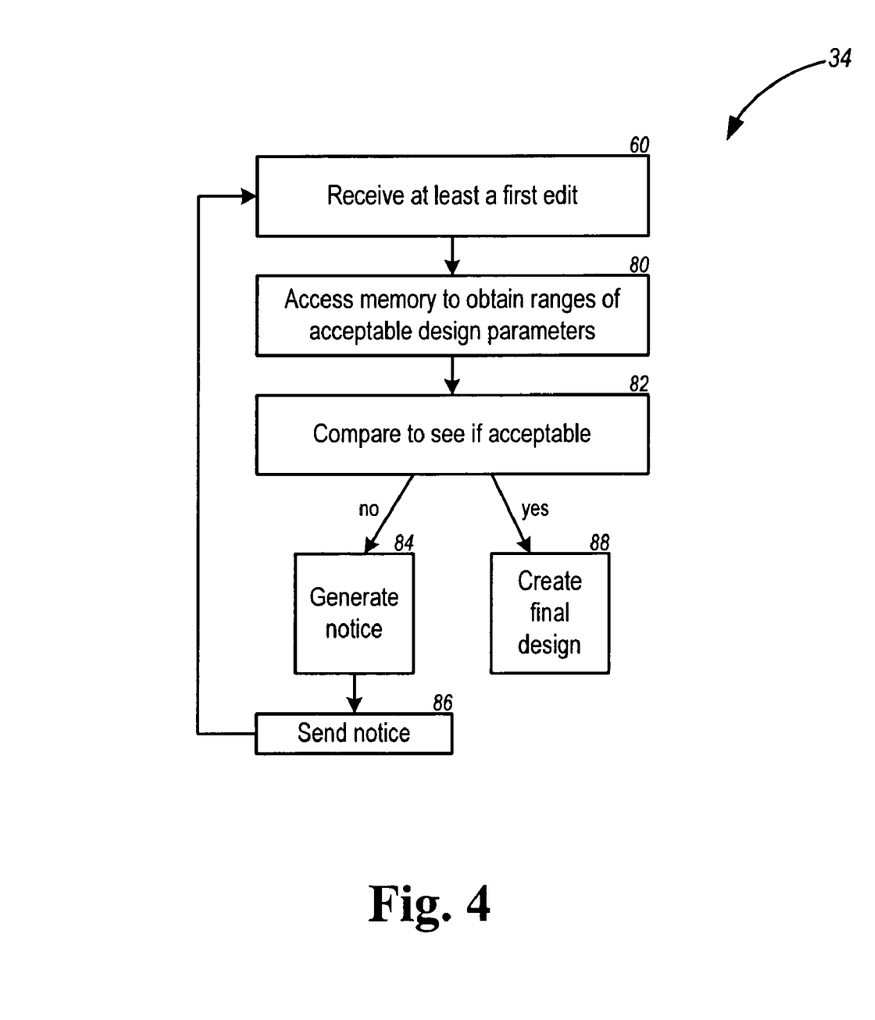
FIG. 4 illustrates a portion of a method of certain embodiments of the invention.

In some embodiments, the automated platform 22 can have tools 26 to ensure that the design is acceptable for treatment of a patient's condition. Not every type of biomedical implant is appropriate for insertion into the human body, and sometimes the surgeon might not be aware of whether a particular design is acceptable. For example, a regulatory agency, such as the Food and Drug Administration, might have determined that a hip stem cannot exceed a certain weight. The surgeon might not be aware of the ranges of acceptable weights, and might have designed an implant with an unacceptable weight. Accordingly, tools 26 can be provided to practice a method, illustrated in FIG. 4, to ensure that the design is acceptable for treatment of a patient's condition. In some embodiments there can be ranges of acceptable design parameters 44 to identify whether an edit 30 is acceptable. In step 80 of the illustrated embodiment, the automated platform 22 can access memory 24 to obtain the ranges of acceptable design parameters 44. Next, in step 82 of certain embodiments, the automated platform 22 can compare the edit 30 to the ranges of acceptable design parameters 44 to determine if the edit 30 is acceptable. If the edit 30 is not acceptable, then in step 84 the automated platform 22 can generate a notice, and in step 86 the automated platform 22 can send the notice to the server 20, and in turn to the surgeon's device 12. The notice informs the surgeon that the edit 30 is not acceptable, and can provide the surgeon with an opportunity to enter another edit. In some embodiments the automated platform 22 is further enabled to repeat the process as needed by comparing any successive edits to the ranges of acceptable design parameters 44. If the edit 30 is acceptable, then in some embodiments the automated platform 22 can create a final design for the biomedical implant, or can provide the surgeon with an opportunity to enter another edit. Accordingly, in some embodiments the automated platform 22 can compare an edit 30 to ranges of acceptable design parameters 44.

Figure 5:
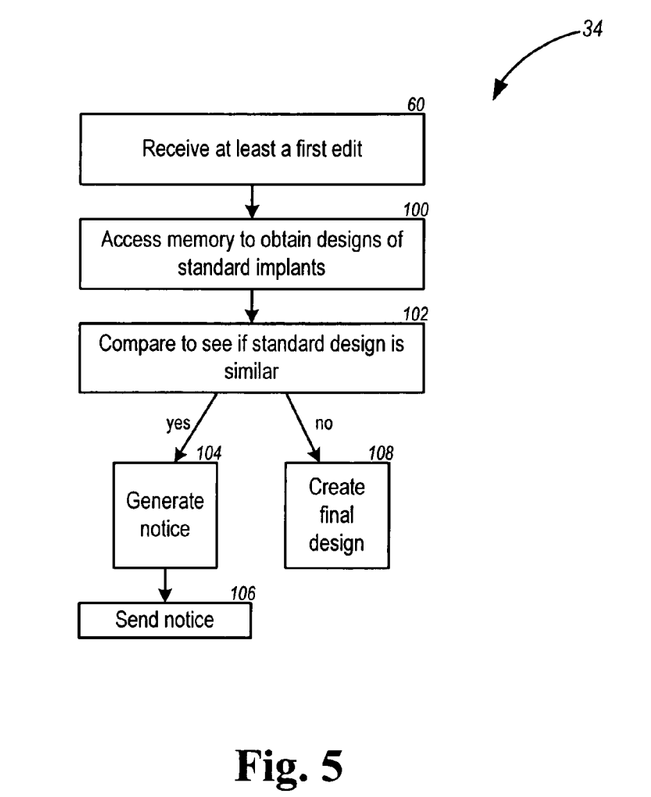
FIG. 5 illustrates another portion of a method of certain embodiments of the invention.

Alternatively, in some embodiments, the automated platform 22 can have tools 26 to compare an edit 30 to the design of a standard biomedical implant 46. Biomedical implant manufacturers have available a wide variety of standard biomedical implants. Sometimes the surgeon might not be aware that a standard implant is suitable for his/her application. The surgeon might find it desirable to obtain a standard implant because a standard implant is less expensive and more readily available than a customized implant. Accordingly, tools 26 can be provided to practice a method, illustrated in FIG. 5, to notify the surgeon that a standard implant might be acceptable for the application. In step 100 of certain embodiments, the automated platform 22 can access memory 24 to obtain designs of standard implants 46. Next, in step 102 of certain embodiments, the automated platform 22 can compare the edit 30 to the designs of standard implants 46. If the edit 30 is substantially similar to a design of a standard implant 46, then in step 104 the automated platform 22 can generate a notice, and in step 106 the automated platform 22 can send the notice to the server 20, and in turn to the surgeon's device 12. The notice can inform the surgeon that a standard implant is similar to the edit 30, and can provide the surgeon with an opportunity to obtain the standard implant. If the edit 30 is not substantially similar to the design of a standard implant 46, then in step 108 of certain embodiments the automated platform 22 can create a final design, or can provide the surgeon with an opportunity to enter another. Accordingly, in some embodiments the automated platform can compare the edit 30 to the designs of standard implants 46.

In certain embodiments the automated platform 22 is further enabled to generate manufacturing instructions 36 to manufacture the implant 40. The manufacturing instructions 36 can include computer aided manufacturing ("CAM") instructions. The manufacturing instructions 36 can be sent to a manufacturing facility 38. In certain embodiments the server 20 and the network 18 can send the manufacturing instructions 36 to the manufacturing facility 38, while in other embodiments the manufacturing instructions 36 can be sent by other means, such as by mail or courier. The manufacturing facility 38 can include standard machine equipment to manufacture implants. When the biomedical implant 40 is completed, the manufacturing facility 38 can send the implant 40 to the surgeon. In some embodiments, the biomedical implant 40 can be sent by the mail.

Referring now to FIGS. 1-2, certain methods of the invention will now be discussed. In step 50 of the illustrated embodiment the surgeon uses the surgeon's device 12 to enter information 14, such as patient data or diagnostic data, and forms a request 28 for a template 32 that represents a biomedical implant. In some embodiments, there can be memory associated with the surgeon's device 12, and the memory can be provided with multiple types biomedical implant templates 42. The surgeon's device 12 can access the memory, and can retrieve the specific template 32 that corresponds to the request 28. In other embodiments such as illustrated in step 52, the surgeon's device 12 transmits the information 14 and the request 28 for a template 32 to the server 20, which in turn transmits to the automated platform 22. In step 54 of some embodiments, the automated platform 22 can then accesses memory 24. The information 14 can be stored in memory 24 to keep a record of the surgeon's order for a biomedical implant 40. In this manner, the information 14 can be recalled if the surgeon needed to temporarily pause the order, or if the surgeon needed to reopen the order once completed. In certain embodiments the memory 24 can store multiple types biomedical implant templates 42, and can obtain the template 32 that corresponds to the surgeon's request 28. In step 56 of some embodiments, the memory 24 can then deliver the template 32 to the automated platform 22, which in turn can transmit the template 32 to the server 20, which in turn can transmit the template 32 to the surgeon's device 12.

In step 58 of certain embodiments, the surgeon can use tools 16 for editing that are accessible by the surgeon's device 12 to create at least a first edit 30 to the template 32. The tools 16 can be provided on the surgeon's device 12, or can be provided on the automatic platform 22 or the server 20 and can be accessible by the surgeon's device 12. As discussed above, embodiments of the invention can provide tools 16 for editing comprising at least one of a slideable bar 110, a menu 112, a blank field 114, a selector 116, or a combination of any of these. Whatever embodiment of the tool 16 for editing is provided, in step 58 the surgeon can use the tool 16 to generate at least a first edit 30 on the template 32. In step 60 of certain embodiments, the at least a first edit 30 can be transmitted to the server 20, which in turn can transmit the at least a first edit 30 to the automated platform 22.

In step 62 of certain embodiments, the automated platform 22 can use tools 26 to generate at least a first response 34. As discussed above, in some embodiments the at least a first response 34 can be to translate the at least a first edit 30 into an at least a first design (not shown). In the embodiment illustrated in FIG. 4, the at least a first response 34 can be to ensure that the design is acceptable for treatment of a patient's condition. In step 84 of FIG. 4, the automated platform 22 can generate a notice if the at least a first edit 30 falls outside of the ranges of acceptable design parameters 44. Alternatively, in the embodiment illustrated in FIG. 5, the at least a first response 34 can be to compare the at least a first design 30 to the designs of standard implants 46. The automated platform 22 can generate a notice if the at least a first edit 30 is substantially similar to the design parameters of standard implants 46. In still other embodiments, the at least a first response 34 can be a combination of any of these responses. Still other responses are within the scope of the invention. In step 64 of certain embodiments, the at least a first response 34 can be transmitted to the server 20, which in turn can transmit the at least a first response 34 to the surgeon's device 12.

In step 66 of certain embodiments, the surgeon's device 12 can either use the tools 16 for editing to generate at least a second edit (not shown), or can generate approval of the design (not shown). If the at least a first response 34 was to generate at least a first design, then the surgeon could give approval of the design. Alternatively, the surgeon might not be satisfied with the at least a first design, and can use the tools 16 for editing to generate at least a second edit. If the at least a first response 34 was to generate notice that at least a first edit 30 falls outside of the ranges of acceptable design parameters 44, then the surgeon can use the tools 16 for editing to generate at least a second edit. Finally, if the at least a first response 34 was to generate notice that the at least a first edit 30 is substantially similar to the design of a standard implant 46, then the surgeon can give approval for the standard implant. In step 68 of certain embodiments, the approval or the second edit can be transmitted to the server 20, which in turn can transmit the approval or the second edit to the automated platform 22. As indicated in FIG. 3, embodiments of the invention allow for repetition of steps 62 through 68 on successive edits by the surgeon's device 12.

In step 70 of certain embodiments, the automated platform 22 can create a final design (not shown). The final design is the product of the collaboration of the surgeon and the biomedical implant manufacturer. The surgeon contributed the at least a first edit 30, and the automated platform 22 of the biomedical implant manufacturer contributed at least a first response 34. In step 72 of certain embodiments, the automated platform 22 can create manufacturing instructions 36 to enable a manufacturing facility 38 to manufacture the implant, if desired. In step 74 of some embodiments, the automated platform 22 can send the manufacturing instructions 36 to a manufacturing facility 38. In certain embodiments the server 20 can send the manufacturing instructions 36 to the manufacturing facility 38, while in other embodiments the manufacturing instructions 36 can be sent by other means, such as by mail or courier. In step 76 of some embodiments, the manufacturing facility 38 can make the implant 40, and in step 78 of some embodiments, the manufacturing facility 38 can send the implant 40 to the surgeon. The implant 40 can be sent to the surgeon by many means, including for example through the mail or courier.

The foregoing is provided for purposes of illustration and disclosure of a preferred embodiment of the invention. Changes, deletions, additions, and modifications may be made to the structures disclosed above without departing from the scope or spirit of the present invention.

The invention claimed is:

1. A method of customizing a biomedical implant for a specific patient from a template, the method comprising:
   a) in an automated platform for design of biomedical implants, receiving a request for a biomedical implant from a surgeon's device adapted to communicate with the automated platform;
   b) accessing memory of the automated platform to obtain a template corresponding to the request, wherein the template is not based on any images representative of the specific patient's anatomy;
   c) automatically transmitting the template to the surgeon's device;
   d) providing a tool for editing the template using the surgeon's device;
   e) receiving at least a first edit of the template from the surgeon's device;
   f) automatically generating at least a first response to the at least a first edit;
   g) automatically transmitting the at least a first response to the surgeon's device;
   h) receiving approval from the surgeon's device; and
   i) automatically creating a final design for the biomedical implant.

2. The method as in claim 1, the first response comprising at least automatically translating the at least a first edit into an at least a first design for a biomedical implant.

3. The method as in claim 1, the first response comprising at least accessing memory of the automated platform to obtain an acceptable range of design parameters and automatically generating a notice if the at least a first edit falls outside of the acceptable range.

4. The method as in claim 1, wherein the template comprises a generic template.

5. The method as in claim 1, where the tool is provided on at least one of the surgeon's device or the automated platform.

6. The method as in claim 1, where the tool comprises at least one of a slideable bar associated with an edge of the template, or a form to input design parameters.

7. The method as in claim 1, where the template is for an intramedullary nail and the tool is adapted to enable editing of at least one of the length, outside diameter, bow radius, hole size, hole location, hole angle, the number of holes, slot size, slot location, material, surface finish, or surface coating.

8. The method as in claim 1, where the template is for a hip stem and the tool is adapted to enable editing of at least one of the profile, stem size, length, head offset, neck height, neck angle, medial and lateral fill, posterior and anterior fill, shoulder height, beam thickness, material, surface finish, or surface coating.

9. The method as in claim 1, further comprising providing a tool for comparison of the final design to diagnostic data.

10. The method as in claim 1, further comprising generating machine instructions and sending the machine instructions to manufacturing facility.

11. The method as in claim 10, further comprising manufacturing the biomedical implant and sending the biomedical implant to the surgeon.

12. A method of customizing a biomedical implant for a specific patient from a template, the method comprising:
   a) in an automated platform for design of biomedical implants, receiving a request for a biomedical implant from a surgeon's device which device is adapted to communicate with the automated platform, wherein the request does not comprise an image representative of the specific patient's anatomy;
   b) accessing memory of the automated platform to obtain a template corresponding to the request;
   c) automatically transmitting the template to the surgeon's device;
   d) providing a tool for editing the template using the surgeon's device;
   e) receiving at least a first edit of the template from the surgeon's device;
   f) accessing memory of the automated platform to obtain an acceptable range of design parameters and automatically generating a notice if the at least a first edit falls outside of the acceptable range;
   g) automatically transmitting the notice to the surgeon's device;
   h) receiving approval from the surgeon's device; and
   i) automatically creating a final design for the biomedical implant.

13. The method as in claim 12, where the tool comprises at least one of a slideable bar associated with an edge of the template or a form to input design parameters.

14. The method as in claim 12, further comprising generating machine instructions and sending the machine instructions to manufacturing facility.

15. The method as in claim 14, further comprising manufacturing the biomedical implant and sending the biomedical implant to the surgeon.

16. The method as in claim 12, further comprising repeating steps (e) through (g) on at least a second edit.

17. A method of customizing a biomedical implant for a specific patient from a generic template, the method comprising:
   a) in an automated platform for design of biomedical implants, receiving a request for a biomedical implant from a surgeon's device which device is adapted to communicate with the automated platform;
   b) accessing memory of the automated platform to obtain a generic template corresponding to the request, wherein the generic template is not based on any images representative of the specific patient's anatomy;

c) automatically transmitting the generic template to the surgeon's device;
d) providing a tool for editing the generic template in order to customize the generic template to the specific patient's anatomy using the surgeon's device;
e) receiving at least a first edit of the generic template from the surgeon's device;
f) accessing memory of the automated platform to obtain designs of standard biomedical implants;
g) automatically generating a notice if the at least a first edit is substantially similar to the design of a standard biomedical implant;
h) automatically transmitting the notice to the surgeon's device;
i) receiving approval from the surgeon's device; and
j) automatically creating a final design for the biomedical implant.

18. The method as in claim 17, where the tool for editing comprises at least one of a slideable bar associated with an edge of the generic template or a form to input the at least one design parameter.

19. The method as in claim 17, further comprising automatically generating machine instructions and sending the machine instructions to manufacturing facility.

20. The method as in claim 19, further comprising manufacturing the biomedical implant and sending the biomedical implant to the surgeon.

21. A method of customizing a biomedical implant for a specific patient from a template, the method comprising:
a) receiving a request for a biomedical implant from a surgeon's device which device is communicatively linked with an automated platform for design of biomedical implants;
b) accessing memory to obtain a template corresponding to the request, wherein the template is not based on any images representative of the specific patient's anatomy;
c) providing a tool for editing the template using the surgeon's device; where the tool comprises at least one of a slideable bar associated with an edge of the template or a form to input design parameters;
d) receiving at least a first edit of the template from the surgeon's device;
e) automatically generating at least a first response to the at least a first edit;
f) automatically transmitting the at least a first response to the surgeon's device;
g) receiving approval from the surgeon's device; and
h) automatically creating a final design for a biomedical implant.

22. The method as in claim 21, the first response comprising at least automatically translating the at least a first edit into an at least a first design for the biomedical implant.

23. The method as in claim 21, the first response comprising at least accessing memory to obtain an acceptable range of design parameters and automatically generating a notice if the at least a first edit falls outside of the acceptable range.

24. The method as in claim 21, further comprising providing particular design parameters in the second form in response to the design parameters selected in the first form.

25. The method as in claim 21, further comprising providing a tool for comparison of the final design to diagnostic data.

26. The method as in claim 21, further comprising generating machine instructions and sending the machine instructions to manufacturing facility.

27. The method as in claim 26, further comprising manufacturing the implant and sending the implant to the surgeon.

28. The method as in claim 21, further comprising repeating steps (e) through (g) on at least a second edit.

29. The method as in claim 21, where the template is for an intramedullary nail and the tool is adapted to enable editing of at least one of the length, outside diameter, bow radius, hole size, hole location, hole angle, the number of holes, slot size, slot location, material, surface finish, or surface coating.

30. The method as in claim 21, where the template is for a hip stem and the tool is adapted to enable editing of at least one of the profile, stem size, length, head offset, neck height, neck angle, medial and lateral fill, posterior and anterior fill, shoulder height, beam thickness, material, surface finish, or surface coating.

31. A method of customizing a biomedical implant for a specific patient from a template, the method comprising:
a) in an automated platform for design of biomedical implants, receiving a request for a biomedical implant from a surgeon's device which device is adapted to communicate with the automated platform, wherein the request does not comprise an image representative of the specific patient's anatomy;
b) accessing memory of the automated platform to obtain a template corresponding to the request;
c) automatically transmitting the template to the surgeon's device;
d) providing a tool for editing the template using the surgeon's device;
e) receiving at least a first edit of the template from the surgeon's device;
f) automatically generating at least a first response to the at least a first edit;
g) automatically transmitting the at least a first response to the surgeon's device;
h) receiving approval from the surgeon's device;
i) automatically creating machine instructions and sending the machine instructions to a manufacturing facility; and
j) manufacturing the biomedical implant and sending the biomedical implant to the surgeon.

32. The method as in claim 31, where the tool for editing comprises at least one of a slideable bar associated with an edge of the template or a form to input design parameters.

33. The method as in claim 31, the first response comprising at least translating the at least a first edit into an at least a first design for a biomedical implant.

34. The method as in claim 31, further comprising repeating steps (e) through (g) on at least a second edit.

35. A system for customizing a biomedical implant for a specific patient from a template, the system comprising:
a) a template for a biomedical implant, wherein the template is not based on any images representative of the specific patient's anatomy;
b) a tool for editing of the template in order to customize the template to the specific patient's anatomy, wherein the tool is accessible by a surgeon's device;
c) an automated platform enabled to receive at least a first edit of the template from the surgeon's device and to automatically generate at least a first response; and
d) a server to communicatively link at least the surgeon's device and the automated platform.

36. The system as in, claim 35, where the tool comprises at least one of a slideable bar associated with an edge of the template, or a form to input design parameters.

37. The system as in claim 35, where the tool is provided on at least the surgeon's device or the automated platform and is accessible by the surgeon's device.

38. The system as in claim 35, the first response comprising at least automatically translating the at least a first edit into an at least a first design for a biomedical implant.

39. The system as in claim 35, the first response comprising at least accessing memory of the automated platform to obtain an acceptable range of design parameters and generating a notice if the at least a first edit falls outside of the acceptable range.

40. The system as in claim 35, wherein the template is for a hip stem and the tool is adapted to edit at least one of the profile, stem size, length, head offset, neck height, neck angle, medial and lateral fill, posterior and anterior fill, shoulder height, beam thickness, material, surface finish, or surface coating.

41. The system as in claim 35, further comprising a tool for comparison of the at least a first design to diagnostic data, wherein the tool for comparison is accessible by a surgeon's device.

42. The system as in claim 35, where the automated platform is further enabled to generate machine instructions, and further comprising a manufacturing facility to manufacture the biomedical implant and send the biomedical implant to the surgeon.

43. A system for customizing a biomedical implant for a specific patient from a template, the system comprising:
   a) a template for a biomedical implant, wherein the template is not based on any images representative of the specific patient's anatomy;
   b) a tool for editing of the template, the tool comprising at least one of a slideable bar associated with an edge of the template or a menu for inputting design parameters, wherein the tool is accessible by a surgeon's device;
   c) an automated platform enabled to receive at least a first edit of the template from the surgeon's device and to automatically translate the at least a first edit into an at least a first design for a biomedical implant; and
   d) a server to communicatively link at least the surgeon's device and the automated platform.

44. The system as in claim 43, where the automated platform is further enabled to access memory to obtain an acceptable range of design parameters and to automatically generate a notice if the at least a first edit falls outside of the acceptable range.

45. The system as in claim 43, wherein the template is for a hip stem and the tool is adapted to edit at least one of the profile, stem size, length, head offset, neck height, neck angle, medial and lateral fill, posterior and anterior fill, shoulder height, beam thickness, material, surface finish, or surface coating.

46. The system as in claim 43, where the automated platform is further enabled to generate machine instructions, and further comprising a manufacturing facility to manufacture the implant and send the implant to the surgeon.

47. A system for customizing a biomedical implant for a specific patient from a generic template, the system comprising:
   a) a generic template for a biomedical implant, wherein the generic template is not based on any images representative of the specific patient's anatomy;
   b) a tool for editing of the generic template in order to customize the generic template to the specific patient's anatomy, wherein the tool is accessible by a surgeon's device;
   c) an automated platform enabled to receive at least a first edit of the generic template from the surgeon's device and to automatically generate a notice if the at least a first edit is substantially similar to the design of a standard biomedical implant;
   d) a server to communicatively link at least the surgeon's device and the automated platform.

48. A system for customizing a biomedical implant for a specific patient from a generic template, the system comprising:
   a) a generic template for a biomedical implant, wherein the generic template is not based on any images representative of the specific patient's anatomy;
   b) a tool for editing of the generic template in order to customize the generic template to the specific patient's anatomy, wherein the tool is accessible by a surgeon's device;
   c) an automated platform enabled receive at least a first edit of the generic template from the surgeon's device and to automatically generate a notice if the at least a first edit falls outside of an acceptable range of design parameters;
   d) a server to communicatively link at least the surgeon's device and the automated platform.

* * * * *